United States Patent [19]
Purtell et al.

[11] 4,325,060
[45] Apr. 13, 1982

[54] FLOATING WATER DETECTOR

[76] Inventors: Jack L. Purtell; Rufus J. Purtell, both of P.O. Box 1152, Brownfield, Tex. 79316

[21] Appl. No.: 104,146

[22] Filed: Dec. 17, 1979

[51] Int. Cl.³ .................... G08B 21/00; G08B 3/10
[52] U.S. Cl. .................... 340/604; 340/605; 340/620; 340/693; 340/384 E
[58] Field of Search .......... 340/602, 604, 605, 620, 340/623, 624, 625, 693, 384 E; 310/324; 200/61.04, 61.05, 61.06

[56] References Cited

U.S. PATENT DOCUMENTS

| | | | |
|---|---|---|---|
| 1,772,232 | 8/1930 | Vanguilder | 340/604 X |
| 2,229,036 | 1/1941 | Bird et al. | 340/605 X |
| 2,726,294 | 12/1955 | Kroening et al. | 340/604 X |
| 3,199,095 | 8/1965 | Ashida | 340/604 |
| 3,331,970 | 7/1967 | Dundon et al. | 310/324 |
| 3,562,731 | 2/1971 | Hsu | 200/61.04 X |
| 3,758,855 | 9/1973 | Meyer | 340/693 X |
| 3,879,726 | 4/1975 | Sweany | 310/324 X |
| 3,889,247 | 6/1975 | Voll | 340/693 x |
| 4,122,365 | 10/1978 | Stephens | 310/324 |
| 4,169,261 | 9/1979 | Alpaugh | 340/693 X |
| 4,178,589 | 12/1979 | Nunn et al. | 340/604 X |
| 4,203,097 | 5/1980 | Manning | 340/620 X |
| 4,227,190 | 10/1980 | Kelley et al. | 340/620 X |

FOREIGN PATENT DOCUMENTS 806192 12/1936 France .................... 340/605

*Primary Examiner*—John W. Caldwell, Sr.
*Assistant Examiner*—Daniel Myer
*Attorney, Agent, or Firm*—Wendell Coffee

[57] ABSTRACT

A moisture detector comprises a shell adapted to float with an anode and cathode on the bottom portion thereof. The anode may be of sacrificial metal which is electrolyzed to increase the conductivity of moisture contacting the electrodes. Also, a water soluble electrolyte may be placed either on the electrodes or close thereto. A plug on the shell may provide for a pair of remote electrodes. A piezoelectric transducer system of improved design involves shaping of the chambers in said shell.

1 Claim, 9 Drawing Figures

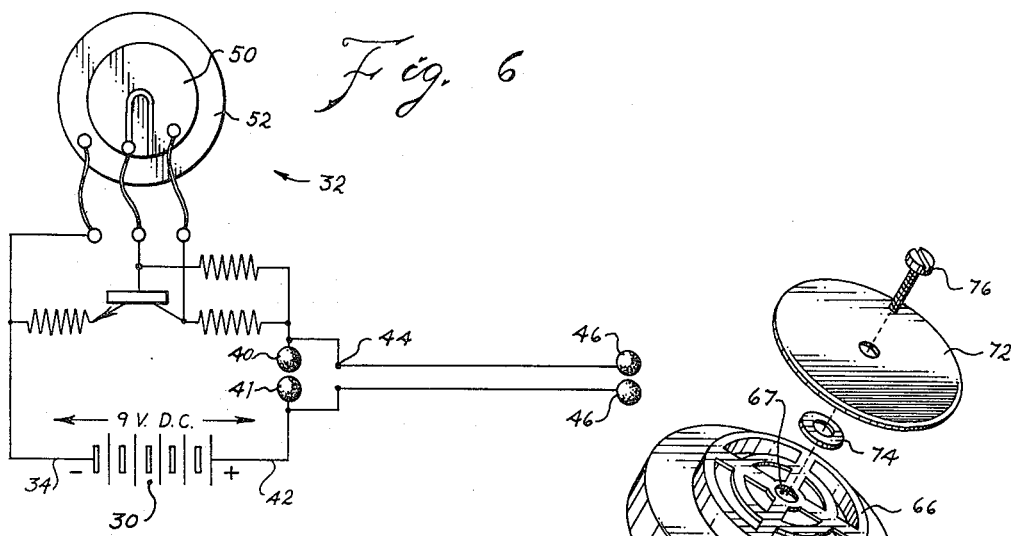
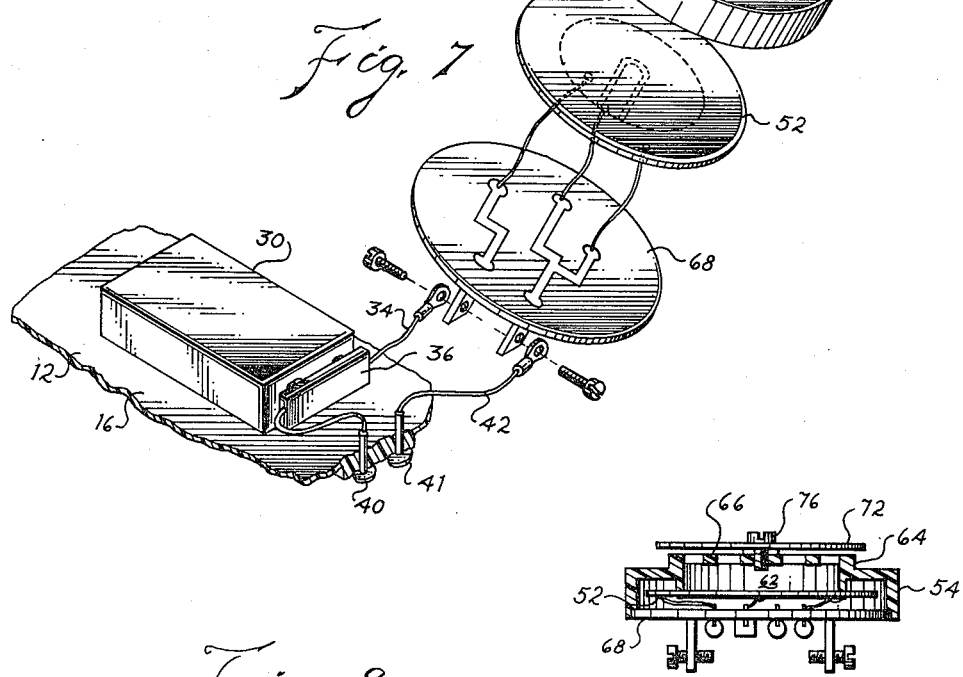
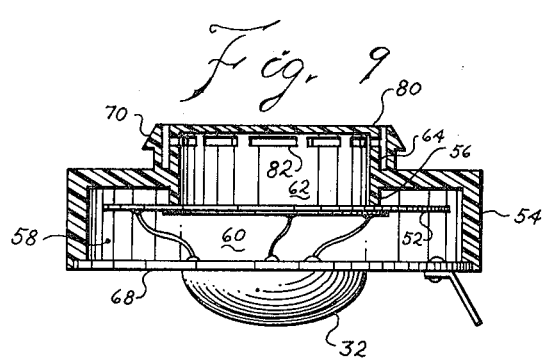

FLOATING WATER DETECTOR

TECHNICAL FIELD

This invention primarily relates to electric alarms which are activated by the presence of moisture and also improved piezoelectric sonic transducers.

BACKGROUND ART

Water leaks are often associated with plumbing fixtures such as hot water heaters, dishwashers, and bathroom fixtures. Many water leaks may go undetected for days, during which time great damage is done such as to carpets in homes. It is desirable to detect water leaking into a boat. Prior workers have used an expansion material in a confined space so that it expands, upon water contact, to push one electrical contact against another. Others, such as EHLIG, U.S. Pat. No. 3,200,388, disclose a material which dissolves upon contact with moisture, such as a salt tablet, and which permits electrical contacts to close. Others, such as HATFIELD, U.S. Pat. No. 4,020,478, have detected the presence of water by conductivity.

Likewise, sonic transducers have been developed. Currently on the market is such a transducer, SONALERT, a registered trademark of P. R. Mallory & Co., Inc. made under the POTTER U.S. Pat. No. 3,277,465, which discloses basic circuits for piezoelectric transducers. Also, the DUNDON ET AL., U.S. Pat. No. 3,331,970 discusses the necessity for matching the acoustic impedance with the transducer impedance. SWEANY ET AL., U.S. Pat. No. 3,890,612, has suggested that a horn of considerable size be placed upon the piezoelectric transducer to aid in its output.

DISCLOSURE OF THE INVENTION

New and Different Function

This invention provides an alarm when there is a water leak by modifying a simple piezoelectric sonic alarm circuit such as a SONALERT (above noted), Model 7930, preferably powered by a 9 volt dc battery. Such device is housed in a polyvinyl chloride (PVC) container sealed to be buoyant in water. Thus, the device, including the modified piezoelectric sonic alarm, is very compact and involves circuits which are extremely simple.

The piezoelectric sonic alarm is further modified by abstracting the front or output chamber of the transducer assembly leaving only very small openings.

Since water often has low conductivity, the conductivity of the water may be increased by providing a soluble electrolyte, such as inorganic salt in the region of sensing electrodes. The conductivity also may be increased by using a sacrificial anode.

The piezoelectric sonic transducer noted above has an extremely high acoustic output impedance as constructed from ceramic ferroelectric materials. Such materials have a very high internal loss and are relatively inefficient. A piezoelectric element made from such materials is attached to drive one end of a short tube or output chamber in most prior units. Such prior units are high impedance sonic piezoelectric transducers. Such high impedance sonic transducers do not work efficiently into the surrounding relatively low impedance atmosphere. That a mismatch exists in such units has been recognized in the prior art such as U.S. Pat. No. 3,331,970. In that case the high impedance of the piezoelectric transducer was lowered by an enclosed chamber loading means which loaded the outer perimeter of the driven piezoelectric disc along with a sonic discharge tube or chamber on the discharge side of the driven sonic element. These and other methods have helped somewhat but still leave an unacceptable high level of mismatch between the low impedance ambient air and the extremely high impedance piezoelectric transducer.

One aspect of this invention is to provide a much improved water detector with a sonic transducer which has a sonic discharge tube or chamber restricted at the discharge end to the extent that the piezoelectric transducer is more perfectly matched, by isolating the low impedance ambient air from the discharge face of the piezoelectric generator. Such improvements are possible only because the generator is highly stable, operating at a frequency of approximately 3000 hertz. By restricting the output chamber the impedance of the output load is effectively raised. Therefore, a more perfect impedance match exists allowing the generator to operate at or near its maximum efficiency.

Further, a water or moisture detector is provided which operates at very low levels of electrical conductivity. The electrical conductivity of the moisture in the region of closely spaced sensing electrodes is changed by providing electrodes made of special metals. When contacted by moisture, electrolysis quickly begins to erode the positive electrode increasing greatly the local conductivity of the moisture. This allows the current to increase between the positive and negative sensing electrodes. By increasing the conductivity the current flow between the sensing electrodes increases greatly to increase the sonic output of the sonic generator.

OBJECTS OF THE INVENTION

An object of this invention is to detect water and to activate an alarm.

Another object of this invention is to increase the audio output of a piezoelectric sonic transducer.

Further objects are to achieve the above with a device that is sturdy, compact, durable, lightweight, simple, safe, efficient, versatile, ecologically compatible, energy conserving, and reliable, yet inexpensive and easy to manufacture, install, adjust, operate and maintain.

Other objects are to achieve the above with a method that is versatile, ecologically compatible, energy conserving, rapid, efficient, and inexpensive, and does not require skilled people to install, adjust, operate, and maintain.

The specific nature of the invention, as well as other objects, uses, and advantages thereof, will clearly appear from the following description and from the accompanying drawing, the different views of which are not scale drawings.

BRIEF DESCRIPTION OF DRAWINGS

FIG. 6 is a schematic representation of the electrical circuitry of the device.

FIG. 7 is an exploded view of the second embodiment of the sonic transducer device.

FIG. 8 is a sectional view of the assembled sonic transducer according to the embodiment of FIG. 7.

FIG. 9 is a sectional view of another embodiment of the sonic transducer device.

DETAILED DESCRIPTION

Figure 1:
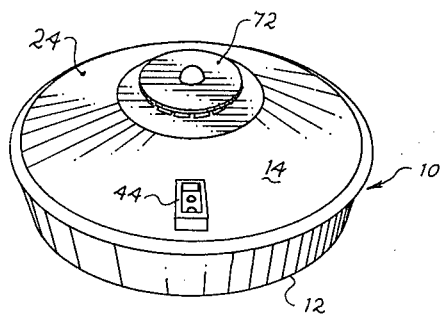
FIG. 1 is a top perspective view of a water detector device according to this invention.
Figure 2:
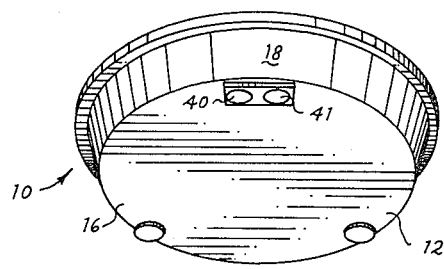
FIG. 2 is a bottom perspective view of a water detector device according to this invention.
Figure 3:
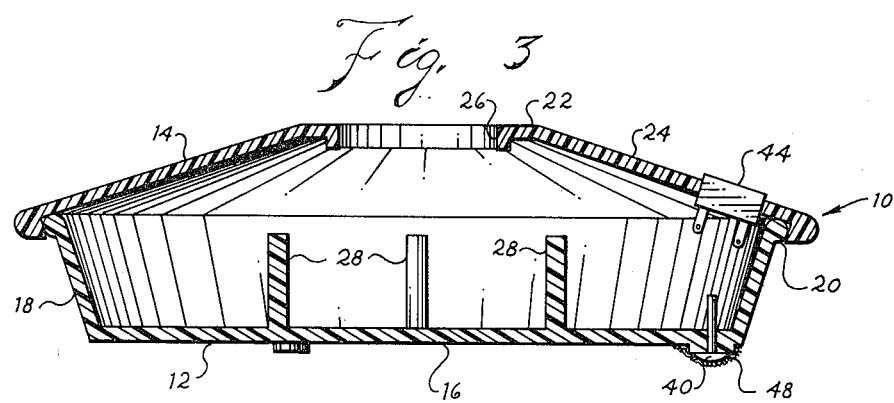
FIG. 3 is an axial sectional view of the shell for the water detector.

Referring to FIGS. 1–4, the water detector comprises a housing or shell 10. Shell 10 includes lower element or hull 12 and upper cover 14. Hull 12 has flat bottom 16 and sloping sides 18 so that the hull has the basic configurations of a pie pan. The top of the sides 18 terminate with a bead 20 which extends outward from the sides slightly. Cover 14 is saucer shaped and has generally sloping or conic edges 24 and a flat top 22 having a circular central aperture 26. Aperture 26 is concentric with the cover 14 and hull 12, both of which are circular in cross section. Preferably, shell 10 is formed of synthetic materials such as polyvinyl chloride.

Hull 12 has four posts 28 projecting upward from the inside of the bottom 16. Posts 28 form a holder for 9 volt battery 30, FIG. 4. A transducer device 32 is attached to the cover 12 at the aperture 26. Battery 30 is heavier than the transducer device 32. Both the transducer device 32 and the battery 30 are centered at the axis of the shell 10 and the weight is concentrated near the bottom of the hull so that hull 12 will float upright in water. Hull 12 has sufficient displacement so that it is buoyant and will float the battery and transducer.

Posts 28 serve to position battery 30 to the bottom 16 of hull 12. Insulated wires 34, extend from terminal cap 36 which serves to complete circuits to the terminals 38 of battery 30. The wire 34 attached to the positive terminal extends to an anode 40 which is one of the water detecting electrodes. Anode 40 extends through the bottom of hull 12 so that anode 40 is exposed on the bottom exterior of hull 12. A cathode 41 is connected by wire 42 to the transducer device 32. A significant feature of the invention is a circuit that assures long life in that it is completely dormant until moisture is present in the region of electrodes 40 and 41. The circuit from battery 30 is non-conductive, avoiding battery drain until moisture bridges the space between the electrodes thereby enabling the alarm unit. The provision of spaced electrodes on the housing surface in series with the battery and the power supply terminals assures positive action when moisture is present. Such control in the low impedance end of the circuit permits simple construction while assuring positive action.

Anode 40 preferably is coated with a sacrificial metal, such as zinc or cadmium. When the shell electrodes 40 and 41 are in contact with moisture, current will flow between the shell electrodes. Often the conductivity of water is rather low, and although the electrodes 40 and 41 are close together current flow may be very low. However, small current flow through the water will electrolyze the coating on anode 40 adding ions to the water and thus greatly increase the conductivity. The metal forming the cathode is not critical and may be copper or it may also be coated with zinc or cadmium thereby standardizing manufacture and simplifying assembly procedures.

Conductivity between electrodes 40 and 41 may also be increased by placing a solid, water soluble electrolyte 48 proximate at least one of the electrodes. By proximate, as used here, what is meant is that it may be on the electrode itself or it may be upon the bottom of the shell 10 adjacent to the electrode. Inorganic salts may be used for this purpose. Copper sulfate is particularly suitable for this purpose. The electrolyte should be non-corrosive and otherwise compatible with the material of the shell electrodes and with the shell itself and to avoid creation of any undesirable stains on carpeting or other supporting structure.

One of wires 34 extends to the anode 40 and the other extends to the transducer device 32. Wire 42 extends from the transducer device 32 to the cathode 41. The transducer device 32 is the sound generator. When moisture bridges electrodes 40 and 41 the alarm is actuated.

In circuit with the shell electrodes 40 and 41 is a plug 44 mounted in cover 14. The terminals of plug 44 are connected, as shown in FIG. 6 as to parallel electrodes 40 and 41 and may thus be connected to remote electrodes 46. By this means, a single unit may be used to detect water at several points, where unit 10 is physically located and where the remote electrodes 46 are placed. A solid, water soluble electrolyte may be placed proximate the remote electrodes 46. Also, the remote electrodes may be coated with a sacrificial material, as described in connection with shell electrodes 40 and 41.

Figure 5:
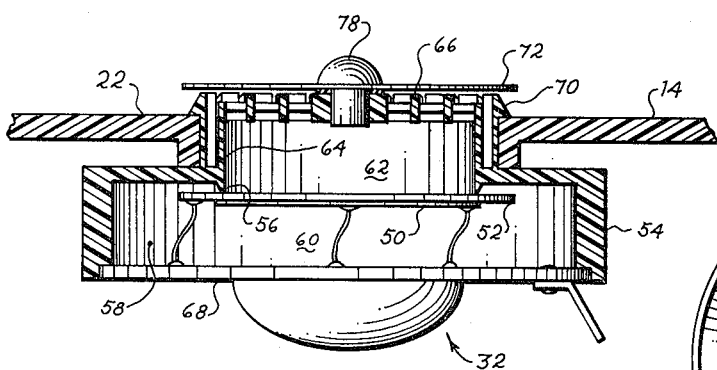
FIG. 5 is a sectional view of a sonic transducer device with circuits and a fragment of the housing.
Figure 4:
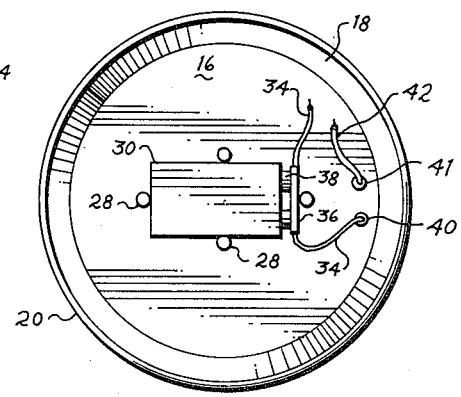
FIG. 4 is a top plan view of the hull of the detector shell with the battery and some wiring in place and the cover removed.

Sonic transducer device 32 is shown in FIG. 5 and may comprise model 7930 SONALERT. Such device is basically the same as disclosed in FIG. 2 of DUNDON ET AL., U.S. Pat. No. 3,331,970. Device 32 includes piezoelectric disc 50 of a given thickness. The piezoelectric disc is attached to a metallic disc 52 having substantially the same thickness as the piezoelectric disc 50 and has a diameter larger than the diameter of disc 50. Discs 50 and 52 are concentric and are fastened together to form a flexible mode sonic transducer assembly having central portions with both elements and a peripheral portion essentially of the portion of the metal disc 52 which extends beyond the piezoelectric disc 50. A housing 54 supports and encloses the transducer assembly. Housing 54 has a support ring 56, which supports the transducer assembly within, but substantially close, to the junction between the central piezoelectric disc 50 and the peripheral portion 52. Housing 54 includes a chamber having a peripheral portion 58 and a central back chamber portion 60. On the front side of disc 52 is an output chamber 62. Chamber 62 is closed on the back by the metallic disc 52. The sides 64 are formed by a tubular extension of support ring 56. A grille 66 on the front of the tube 46 defines the front of output chamber 62.

The electrical circuits of an oscillator which includes disc 50 are mounted on a circuit board 68 which is circular and which is attached to housing 54 to close chamber 58–60. The transducer assembly, particularly the piezoelectric disc 50, closes the other side of the chamber 58–60. Resilient fingers 70 extend around the tube 46 and form a latch means for holding housing 54 in place within aperture 26 of cover 14. Grille 66 has a circular hole through the center of it.

It has been discovered that if the front chamber 62 is substantially closed so that there is a very small opening between a circular cover 72 and the end of the tube 64, the level of the audible output is greatly increased. This is accomplished as seen in FIG. 7. A small rubber washer 74 is aligned with the circular hole 67 in the grille 66. Cover 72 is then attached by screw 76. Proper thickness of washer 74 provides a very definite maximum output. By monitoring the output level by a decibel meter and the current to the sonic transducer device 32 with an amp meter it may be found that there is a particular spacing at which the audio output increases by about 8 to 10 decibels and the power input to the device decreases by about 5%. It has been found that for this unit referred to herein, a preferred spacing will be about 0.030 inch (0.75 mm) where the diameter of the tube 64 is about ⅞ inch (22.0 mm), providing a throat area of 0.08 sq. inches (0.5 sq. cm). This impedance matching loading means works effectively well on various lengths and sizes of output tubes or chambers of the piezoelectric sonic transducers. An impedance match is obtained by securing the disc 72 over the discharge end of the loading chamber or tube and moving it in or out until the optimal impedance loading match occurs. The optimal point of loading is detected by a decrease in power input and a greatly increased sonic output. This means of impedance matching allows the sonic piezoelectric generator to be manufactured with a very short compact discharge chamber or tube without sacrificing the efficiency and sonic output. By this method of impedance matching not only do we increase the sonic output but we also greatly amplify the standing sonic waves which make the sound more sensitive and conspicuous to anyone moving through the sonic standing waves.

Such sonic transducers may be manufactured with the discharge end of the sonic tube or chamber closed except for some small sonic openings peripherally placed and sized to match the impedance of the piezoelectric sonic transducer as will be described.

As may be seen, the embodiment of FIGS. 5, 7 and 8 are given the same reference characters. However, in FIGS. 7 and 8 the latch finger 70 for attaching the sonic device housing 54 within an aperture is not shown and the smooth housing shown in FIG. 5 has not been shown in FIGS. 7 and 8.

Screw 76, FIGS. 7 and 8 provides for adjustability, i.e., to raise or lower the disc 72 to change the size of the opening from output chamber 62. Once it has been determined what opening from the output chamber 62 is optimum to produce the maximum audible output, the cap 72 may be attached by rivet 78, as shown in FIG. 5.

FIG. 9 represents a preferred embodiment if new dies were to be made to cast the housing 54. If only a relatively small number of detectors were being made, the embodiment of FIG. 5 would be the preferred embodiment. If a sufficiently large number of the devices were to be made, the device of FIG. 9 would represent the preferred embodiment.

Basically, the device of FIG. 9 includes the circuit board 68 having the basic circuitry of the transducer device 32. Housing 54 is basically identical to the housing in FIG. 5, i.e., it has back chamber portion 60, peripheral chamber portion 58, ring 56 supporting the transducer assembly, including piezoelectric disc 50 and metallic disc 52. Also, latch fingers 70 are used to hold housing 54 within an aperture. However, in its preferred form, outlet chamber 62 would have the tube 64 closed by integral cover 80. The openings from the output chamber 62 would consist of a plurality of slits 82 at the top of the tube 64. The total area of the slits 82 would be equal to the area of the optimum opening, i.e., about 0.5 sq. cm. for the piezoelectric disc having a metallic disc diameter of about 3.5 cm. Slits 82 are circumferential slits, and are all in the same diametrical plane parallel to and just below the plane of cover 80.

The embodiments shown and described above are only exemplary. Various modifications can be made in the construction, material, arrangement, and operation, and still be within the scope of the invention. The limits of the invention and the bounds of the patent protection are measured by and defined in the following claims. The restrictive description and drawing of the specific example above do not point out what an infringement of this patent would be, but are to enable the reader to make and use the invention.

As an aid to correlating the terms of the claims to the exemplary drawings, the following catalog of elements is provided:

| | |
|---|---|
| 10 shell | 46 remote electrodes |
| 12 hull | 48 electrolyte |
| 14 cover | 50 piezoelectric disc |
| 16 bottom | 52 metallic disc |
| 18 side | 54 sonic housing |
| 20 bead | 56 ring |
| 22 top | 58 peripheral chamber |
| 24 conic edges | 60 back chamber |
| 26 aperture | 62 front chamber |
| 28 post | 64 tube |
| 30 battery | 66 grille |
| 32 transducer device | 67 hole |
| 34 wires | 68 circuit board |
| 36 terminal cap | 70 fingers |
| 38 terminals | 72 cover |
| 40 anode | 74 washer |
| 41 cathode | 76 screw |
| 42 wire | 78 rivet |
| 44 plug | 80 cover |

What is claimed is:
1. A water detector comprising:
a. an enclosure in the form of a shell,
b. said shell including a top and a hull having a flat bottom forming a base of the shell and thus a base of the water detector,
c. a pair of spaced electrodes extending through and exposed on the bottom of the hull, so that the water detector is adapted to rest upon the base of the shell and thus the electrodes,
d. a sonic housing mounted in the shell,
e. an alarm including
 i. a piezoelectric transducer driven by
 ii. an oscillator, and having
 iii. two power supply terminals,
f. said alarm in said sonic housing,
g. a battery having two battery terminals in said shell, and
h. circuit connectors consisting of:
 i. one of the battery terminals solely connected to one of the electrodes,
 ii. the other electrodes solely connected to one of the power supply terminals on the alarm, and
 iii. the other power supply terminal solely connected to the other battery terminal,
j. so that the alarm is activated upon bridging the space between the electrodes by moisture.

* * * * *